United States Patent [19]

Lindel et al.

[11] Patent Number: 4,863,939
[45] Date of Patent: Sep. 5, 1989

[54] HETEROARYLETHYLAMINE AS PRODUCTION PROMOTERS IN LIVESTOCK

[75] Inventors: Hans Lindel, Leverkusen; Werner Hallenbach, Langenfeld; Friedrich Berschauer, Wuppertal; Anno de Jong, Wuppertal; Martin Scheer, Wuppertal, all of Fed. Rep. of Germany

[73] Assignee: Bayer Aktiengesellschaft, Leverkusen, Fed. Rep. of Germany

[21] Appl. No.: 80,284

[22] Filed: Jul. 30, 1987

Related U.S. Application Data

[63] Continuation-in-part of Ser. No. 40,509, Apr. 20, 1987.

[30] Foreign Application Priority Data

Aug. 14, 1986 [DE] Fed. Rep. of Germany ....... 3627663

[51] Int. Cl.$^4$ .................. A61K 31/44; C07D 213/84; C07D 211/72; C07D 211/84
[52] U.S. Cl. .................. 514/357; 514/344; 514/346; 514/348; 514/349; 514/350; 514/351; 514/352; 514/353; 514/354; 514/355; 514/356; 514/338; 546/286; 546/288; 546/289; 546/290; 546/292; 546/293; 546/296; 546/297; 546/298; 546/299; 546/300; 546/304; 546/309; 546/310; 546/312; 546/314; 546/315; 546/316; 546/322; 546/326; 546/328; 546/329; 546/336; 546/335; 546/270
[58] Field of Search ............... 546/314, 315, 316, 322, 546/326, 328, 329, 336, 335, 286, 288, 289, 290, 292, 293, 296, 297, 298, 299, 300, 304, 309, 310, 312, 270; 514/344, 346, 348, 349, 350, 351, 352, 353, 354, 355, 356, 357, 338

[56] References Cited

U.S. PATENT DOCUMENTS

| | | | |
|---|---|---|---|
| 4,088,764 | 5/1978 | Raabe et al. | 546/314 |
| 4,358,455 | 11/1982 | Atkinson et al. | 544/338 |
| 4,761,421 | 8/1988 | Muir | 514/352 |

FOREIGN PATENT DOCUMENTS

| | | | |
|---|---|---|---|
| 0170538 | 2/1986 | European Pat. Off. | 514/352 |
| 0254856 | 2/1988 | European Pat. Off. | 514/352 |
| 2603600 | 10/1976 | Fed. Rep. of Germany | 544/338 |
| 120770 | 10/1984 | Fed. Rep. of Germany | 544/338 |

Primary Examiner—Mary C. Lee
Assistant Examiner—J. Richter

Attorney, Agent, or Firm—Sprung, Horn, Kramer & Woods

[57] ABSTRACT

The growth of livestock is promoted by the new compounds of the formula

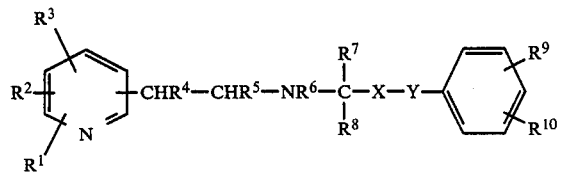

in which
$R^1$ represents hydrogen, alkyl, halogen, halogenoalkyl, hydroxyl, cyano, alkoxycarbonyl, aminocarbonyl, mono- and dialkylaminocarbonyl, alkoxy, halogenoalkoxy, halogenoalkylthio or $NHSO_2$-alkyl,
$R^2$ represents hydrogen, hydroxyl, alkoxy or the $-NR^{11}R^{12}$ radical,
$R^3$ represents the radicals mentioned in the case of $R^1$,
$R^4$ represents hydroxyl, acyloxy or alkoxy,
$R^5$ represents hydrogen or alkyl,
$R^6$ represents hydrogen or alkyl,
$R^7$ represents hydrogen or alkyl,
$R^8$ represents hydrogen or alkyl,
X represents $C_1$-$C_{10}$-alkylene or a direct bond,
Y represents oxygen or a direct bond,
$R^9$ represents hydrogen, $C_1$-$C_{10}$-alkyl which is optionally substituted by hydroxyl, alkoxy, acyloxy or the $-NR^{13}R^{14}$ radical, or represents the $COR^{15}$ radical or the $O-Z-R^{16}$ radical,
Z represents $C_1$-$C_{10}$-alkylene, $C_1$-$C_{10}$-alkenylene or $C_1$-$C_{10}$-alkinylene,
$R^{10}$ represents hydrogen, halogen, alkyl, alkoxy, hydroxyl or the $COR^{15}$ radical,
$R^{11}$ represents hydrogen or alkyl,
$R^{12}$ represents hydrogen, alkyl, halogenoalkyl or acyl,
$R^{13}$ represents hydrogen, optionally substituted alkyl or optionally substituted aryl,
$R^{14}$ represents the radicals mentioned in the case of $R^{13}$,
$R^{15}$ represents hydroxyl, alkoxy or the $NR^{13}R^{14}$ radical, and
$R^{16}$ represents hydroxyl, alkoxy, acyloxy, the $NR^{13}R^{14}$ radical or the $COR^{15}$ radical, and the physiologically acceptable salts and N-oxides thereof. Several new intermediates are also disclosed.

15 Claims, No Drawings

HETEROARYLETHYLAMINE AS PRODUCTION PROMOTERS IN LIVESTOCK

This is a continuation-in-part of application Ser. No. 040,509, filed Apr, 20, 1987, now pending.

The present invention relates to new heteroarylethylamines, processes for the preparation thereof, and the use thereof as production promoters in livestock.

Heteroarylethylamines are already known. They have a beta-sympathomimetic action (DE-OS (German published specification) No. 2,603,600, EP-OS (European published specification) No. 120,770 and U.S. patent specification No. 4,358,955). However, nothing has been disclosed on the suitability of these compounds as production promoters in livestock.

The following have now been found:

1. New compounds of the formula I

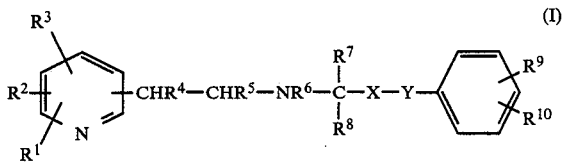

in which
- $R^1$ represents hydrogen, alkyl, halogen, halogenolkyl, hydroxyl, cyano, alkoxycarbonyl, aminocarbonyl, mono- and dialkylaminocarbonyl, alkoxy, halogenoalkoxy, halogenoalkylthio or $NHSO_2$-alkyl,
- $R^2$ represents hydrogen, hydroxyl, alkoxy or the $-NR^{11}R^{12}$ radical,
- $R^3$ represents the radicals mentioned in the case of $R^1$,
- $R^4$ represents hydroxyl, acyloxy or alkoxy,
- $R^5$ represents hydrogen or alkyl,
- $R^6$ represents hydrogen or alkyl,
- $R^7$ represents hydrogen or alkyl,
- $R^8$ represents hydrogen or alkyl,
- X represent $C_1$–$C_{10}$-alkylene or a direct bond,
- Y represents oxygen or a direct bond,
- $R^9$ *represents hydrogen,* $C_1$–$C_{10}$-alkyl which is optionally substituted by hydroxyl, alkoxy, acyloxy or the $-NR^{13}R^{14}$ radical, or represents the $COR^{15}$ radical or the $O-Z-R^{16}$ radical,
- Z represents $C_1$–$C_{10}$-alkylene, $C_1$–$C_{10}$alkenylene or $C_1$–$C_{10}$-alkinylene,
- $R^{10}$ represents hydrogen, halogen, alkyl, alkoxy, hydroxyl or the $COR^{15}$ radical,
- $R^{11}$ represents hydrogen or alkyl,
- $R^{12}$ represents hydrogen, alkyl, halogenoalkyl or acyl,
- $R^{13}$ represents hydrogen, optionally substituted alkyl or optionally substituted aryl,
- $R^{14}$ represents the radicals mentioned in the case of $R^{13}$,
- $R^{15}$ represents hydroxyl, alkoxy or the $NR^{13}R^{14}$ radical, and
- $R^{16}$ represents hydroxyl, alkoxy, acyloxy, the $NR^{13}R^{14}$ radical of the $COR^{15}$ radical, and the physiologically acceptable salts and N-oxides thereof.

2. Process for the preparation of the compounds of the formula I,

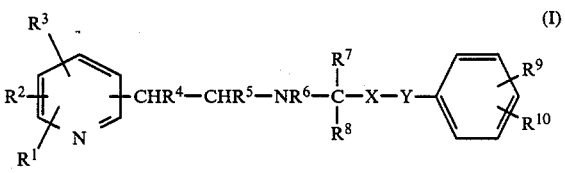

in which
$R^1$ to $R^{10}$, X and Y have the abovementioned meaning, (a) wherein halogenomethyl ketones of the formula II,

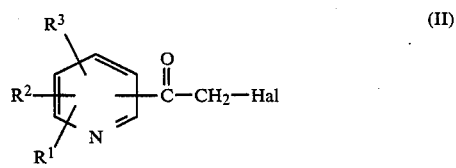

in which
$R^1$, $R^2$ and $R^3$ have the abovementioned meaning and Hal represents halogen,
are reacted with amines of the formula III

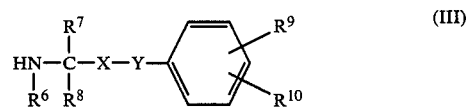

in which
$R^6$ to $R^{10}$, X and Y have the abovementioned meaning,
and the carbonyl group is subsequently reduced, or (b) wherein epoxides of the formula IV

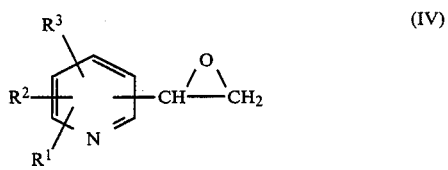

in which
$R^1$, $R_2$ and $R^3$ have the abovementioned meaning,
are reacted with amines of the formula III

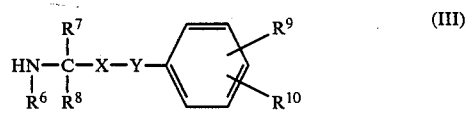

in which
$R^6$ to $R^{10}$, X and Y have the abovementioned meaning, or (c) wherein β-halogenoethyl compounds of the formula V

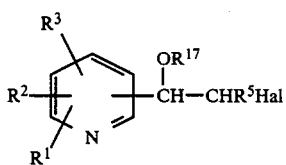

in which
R¹, R², R³ and R⁵ have the abovementioned meaning,
Hal represents halogen, and
R¹⁷ represents hydrogen or $C_1$–$C_4$-alkyl,
are reacted with amines of the formula III

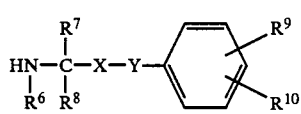

in which
R⁶ to R¹⁰, X and Y have the abovementioned meaning, or (d) wherein, in the case where R⁶ and R⁷ in the formula I represent hydrogen, compounds of the formula VI

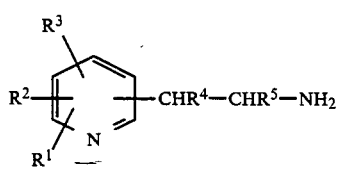

in which
R¹ to R⁵ have the abovementioned meaning,
are reacted with ketones of the formula VII

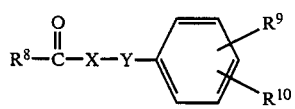

in which
R⁸, R⁹, R¹⁰, X and Y have the abovementioned meaning,
under reducing conditions, or (e) wherein, in the case where R⁴ represents hydroxyl, and R⁵ and R⁶ represent hydrogen in the formula I, compounds of the formula VIII

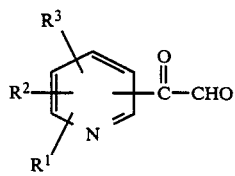

in which
R¹, R² and R³ have the abovementioned meaning,
are reacted with amines of the formula IX

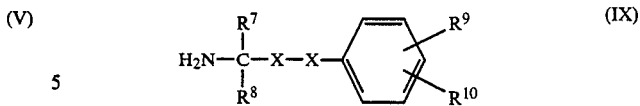

in which
R⁷ to R¹⁰ have the abovementioned meaning, under reducing conditions, or (f) wherein, in the case where R⁴ represents hydroxyl and R⁶ represents hydrogen in the formula I, compounds of the formula X

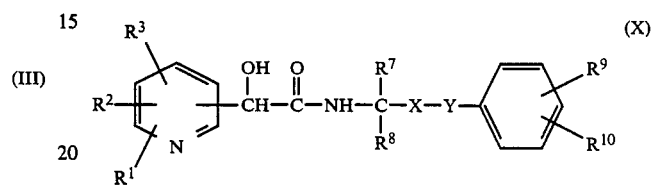

in which
R¹, R², R³, R⁷, R⁸, R⁹, R¹⁰, X and Y have the abovementioned meaning,
are reduced.

3. New compounds of the formula X

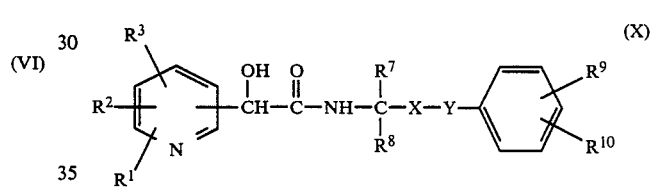

in which
R¹, R², R³, R⁷, R⁸, R⁹, R¹⁰, X and Y have the meanings mentioned in the case of the compounds of the formula I.

4. Process for the preparation of compounds of the formula X, characterized in that compounds of the formula XI

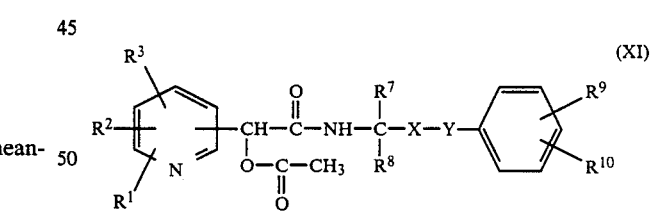

in which
R¹ to R¹⁰, X and Y have the abovementioned meaning,
are hydrolyzed.

5. New compounds of the formula XI

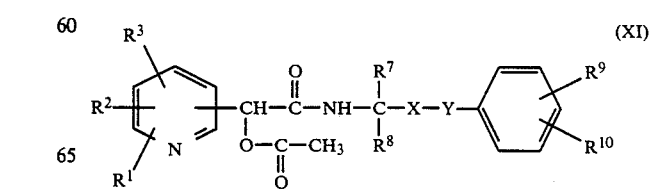

in which $R^1$ to $R^{10}$, X and Y have the abovementioned meaning.

6. Process for the preparation of compounds of the formula XI, characterized in that aldehydes of the formula XII

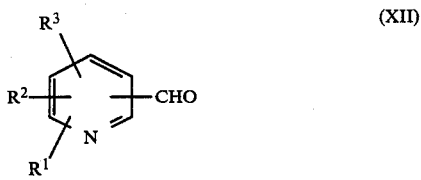

in which $R^1$, $R^2$ and $R^3$ have the abovementioned meaning, are reacted with isonitriles of the formula XIII

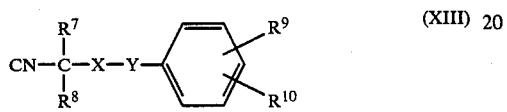

in which $R^7$ to $R^{10}$, X and Y have the abovementioned meaning, in the presence of acetic acid.

The compounds of the formula I may be present in the form of their tautomers. In the case where $R_2$ represents $NH_2$, examples of these are:

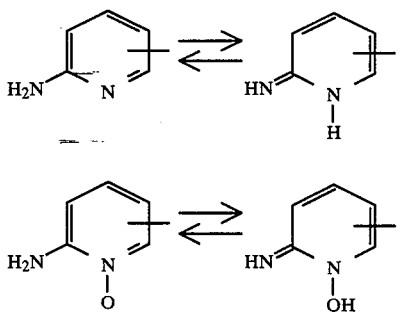

The compounds of the formula I may also be present in the form of their steric and optical isomers, and, in this case, form enantiomeric and/or diastereometric forms to one another.

Physiologically acceptable salts of the compounds of the formula I can be formed with the following acids: hydrochloric acid, sulphuric acid, phosphoric acid, perchloric acid, hydrobromic acid, hydroiodic acid, nitric acid, acetic acid, oxalic acid, malonic acid, succinic acid, ascorbic acid, malic acid, tartaric acid, maleic acid, fumaric acid, methanesulphonic acid, benzoic acid, substituted benzoic acids, formic acid, toluenesulphonic acid, benzenesulphonic acid, phthalic acid, naphthalenesulphonic acid, nicotinic acid, palmitic acid and embonic acid.

Preferred compounds of the formula I are those in which $R^1$ represents hydrogen, $C_{1-4}$-alkyl, fluorine, chlorine, bromine, $C_{1-4}$-halogenoalkyl, hydroxyl, cyano, $C_{1-4}$-alkoxycarbonyl, mono- or di-$C_{1-4}$alkylaminocarbonyl, $C_{1-6}$-alkoxy, $C_{1-6}$-halogenoalkoxy, $C_{1-6}$-halogenoalkylthio or $—NHSO_2—C_{1-6}$-alkyl, $R^2$ represents hydrogen, hydroxyl, $C_{1-6}$-alkoxy or the $—NR^{11}R^{12}$ radical, $R^3$ represents the radicals mentioned in the case of $R^1$, $R^4$ represents OH, $C_{1-6}$-alkoxy or acyloxy and acyloxy represents oxycarbonyl-$C_{1-6}$-alkyl, optionally substituted oxycarbonylphenyl, oxysulphonyl-$C_{1-6}$-alkyl or optionally substituted oxysulphonylphenyl, $R^5$ represents hydrogen or $C_1$–$C_6$-alkyl, $R^6$ represents hydrogen or optionally substituted $C_{1-6}$-alkyl, $R^7$ represents hydrogen or $C_1$–$C_6$-alkyl, $R^8$ represents hydrogen or $C_1$–$C_6$-alkyl, X represents $C_1$–$C_6$-alkylene or a direct bond, Y represents oxygen or a direct bond, $R^9$ represents hydrogen, $C_1$–$C_6$-alkyl which is optionally substituted by hydroxyl, $C_1$–$C_6$-alkoxy, $C_1$–$C_6$-acyloxy or the $NR^{13}R^{14}$ radical, or represents the $COR^{15}$ radical or the $O—Z—R^{16}$ radical, Z represents $C_1$–$C_6$alkylene, $C_2$–$C_6$-alkenylene or $C_2$–$C_6$-alkinylene, $R^{10}$ represents hydrogen, halogen, $C_1$–$C_6$-alkyl, $C_1$–$C_6$-alkoxy, hydroxyl or the $COR^{15}$ radical, $R^{11}$ represents hydrogen or $C_1$–$C_6$-alkyl, $R^{12}$ represents hydrogen, $C_{1-6}$-alkyl, $C_{1-4}$-halogenoalkyl, $C_{1-6}$-alkylcarbonyl or optionally substituted phenylsulphonyl, $R^{13}$ represents hydrogen or $C_1$–$C_6$-alkyl which is optionally substituted, $R^{14}$ represents the radicals mentioned in the case of $R^{13}$, $R^{15}$ represents hydroxyl, $C_1$–$C_6$-alkoxy or the $NR^{13}R^{14}$ radical, and $R^{16}$ represents hydroxyl, $C_1$–$C_6$-alkoxy, $C_1$–$C_6$-acyloxy, the $NR^{13}R^{14}$ radical or the $COR^{15}$ radical.

Suitable substituents of the optionally substituted radicals are preferably: cyano, halogen, such as fluorine or chlorine, hydroxyl, $C_{1-4}$-alkyl, $C_{1-4}$-halogenoalkyl, phenyl, $C_{1-4}$-alkoxy, $C_{1-4}$-halogenoalkoxy, $C_{1-4}$-alkylthio and $C_{1-4}$-halogenoalkylthio, and, in the case where the substituents are on a phenyl radical, additionally preferably methylenedioxy, ethylenedioxy, halogen-substituted methylenedioxy, halogen-substituted ethylenedioxy, and furthermore phenyl or phenoxy which may themselves carry one or more of the abovementioned substituents.

Particularly preferred compounds of the formula I are those in which $R^1$ represents hydrogen, $C_{1-4}$-alkyl, halogen, particularly fluorine, chlorine or bromine, cyano, hydroxyl, $C_{1-4}$-halogenoalkyl having 1 to 5 halogen atoms, $C_{1-4}$-alkoxy, $C_{1-4}$-halogenoalkoxy having 1 to 5 halogen atoms, $NHSO_2—C_{1-4}$-alkyl, $—COO—C_{1-4}$-alkyl, $—CONH_2$, $—CONH—C_{1-4}$-alkyl or $—CON(C_{1-4}$-alkyl), $R^2$ represents hydrogen, OH, $C_{1-4}$-alkoxy or $—NR^{11}R^{12}$, $R^3$ represents the radicals mentioned in the case of $R^1$ $R^4$ represents OH or $C_{1-6}$-acyloxy, particularly acetoxy, $R^5$ represents hydrogen or $C_1$–$C_3$-alkyl, particularly methyl or ethyl, $R^6$ represents hydrogen, $R^7$ represents hydrogen, $R^8$ represents hydrogen or $C_1$–$C_3$-alkyl, particularly methyl or ethyl, X represents $C_1$-$C_3$-alkylene, particularly methylene or ethylene, Y represents a direct bond, $R^9$ represents hydrogen, $C_1$-$C_3$-alkyl which is preferably substituted by hydroxyl, $C_1$-$C_3$-alkoxy, particularly methoxy, $C_1$-$C_3$-acyloxy, particularly acetoxy, or the $NR^{13}R^{14}$ radical, the $COR^{15}$ radical or the O—Z—$R^{16}$ radical, Z represents $C_1$-$C_4$-alkylene, particularly methylene or ethylene, $C_2$-$C_4$-alkenylene or $C_2$-$C_4$-alkinylene, $R^{10}$ represents hydrogen, halogen, particularly fluorine, chlorine or bromine, $C_1$-$C_3$-alkyl, particularly methyl, $C_1$-$C_3$-alkoxy, particularly methoxy, hydroxyl or the $COR^{15}$ radical, $R^{11}$ represents hydrogen or $C_1$-$C_3$-alkyl, particularly methyl or ethyl, $R^{12}$ represents hydrogen or methyl, $R^{13}$ represents hydrogen or $C_1$-$C_3$-alkyl, particularly methyl or ethyl, $R^{14}$ represents hydrogen, $R^{15}$ represents hydroxyl, $C_1$-$C_3$-alkoxy, particularly methoxy or ethoxy, or the $NR^{13}R^{14}$ radical, and $R^{16}$ represents hydroxyl, $C_1$-$C_3$-alkoxy, particularly methoxy, $C_1$-$C_3$-acyloxy, particularly acetoxy, the $NR^{13}R^{14}$ radical or the $COR^{15}$ radical.

The following compounds of the formula I may be mentioned individually in addition to the examples:

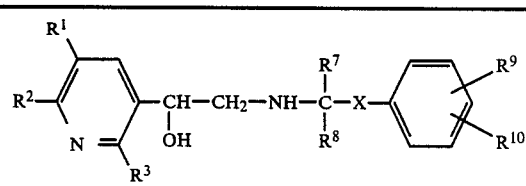

| $R^1$ | $R^2$ | $R^3$ | $R^7$ | $R^8$ | X | $R^9$ | $R^{10}$ |
|---|---|---|---|---|---|---|---|
| Cl | $NH_2$ | H | H | $CH_3$ | —$CH_2$— | H | 3-Cl |
| CN | $NH_2$ | H | H | H | —$CH_2$— | 4-$CH_3$ | H |
| Cl | OH | H | $CH_3$ | H | —$(CH_2)_2$— | 4-$COOCH_3$ | 3-Cl |
| CN | OH | H | $C_2H_5$ | H | —$(CH_2)_2$— | 4-$OCH_2$—$COOCH_3$ | 2-Br |
| H | $NH_2$ | H | $CH_3$ | H | —$CH_2$— | 4-$OCH_2$—$COOCH_3$ | H |
| H | $NH_2$ | H | H | H | —$CH_2$—H | 4-$COOCH_3$ | |

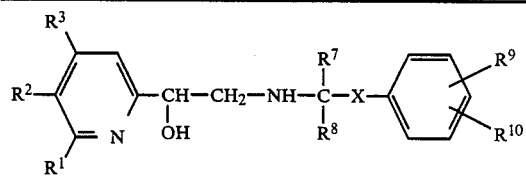

| $R^1$ | $R^2$ | $R^3$ | $R^7$ | $R^8$ | X | $R^9$ | $R^{10}$ |
|---|---|---|---|---|---|---|---|
| Cl | $NH_2$ | Cl | H | H | —$CH_2$— | 4-$OCH_2CH_2OH$ | 3-$CH_3$ |
| Cl | $NH_2$ | Cl | $CH_3$ | H | —$(CH_2)_2$— | 4-$OCH_2COOCH_3$ | H |
| Cl | $NH_2$ | Cl | H | $C_2H_5$ | —$CH_2$ | 4-$OCH_2COOH$ | 2-Cl |
| Cl | $NH_2$ | Cl | $C_2H_5$ | $CH_3$ | —$(CH_3)_3$— | 4-$COOC_2H_5$ | H |
| Cl | $NH_2$ | CN | $CH_3$ | H | —$CH_2$— | 4-$OCH_2CH_2NH_2$ | H |
| CN | $NH_2$ | Cl | H | $CH_3$ | —$(CH_2)_2$— | 4-$COOCH_3$ | H |
| Cl | $NH_2$ | CN | H | H | —$CH_2$— | 4-$OCH_2COOCH_3$ | 2-Br |
| CN | $NH_2$ | H | H | $CH_2$ | —$CH_2$— | 4-$OCH_2COOCH_3$ | H |
| H | $NH_2$ | CN | $CH_3$ | H | —$(CH_2)_2$ | 4-$COOCH_3$ | 3-Cl |
| Br | $NH_2$ | CN | H | $CH_3$ | —$CH_2$— | 4-$OCH_2COOH$ | H |

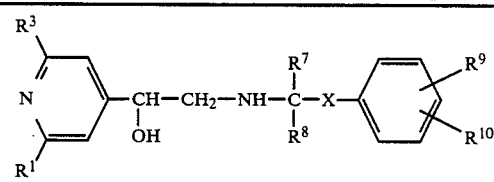

| $R^1$ | $R^3$ | $R^7$ | $R^8$ | X | $R^9$ | $R^{10}$ |
|---|---|---|---|---|---|---|
| Cl | Cl | H | $CH_3$ | —$CH_2$— | 4-$OCH_2COOCH_3$ | H |
| Cl | Cl | $CH_3$ | H | —$CH_2$— | 4-$OCH_2COOH$ | H |
| CN | H | H | $CH_3$ | —$CH_2$— | 4-$OCH_2COOCH_3$ | H |
| Cl | H | H | $C_2H_5$ | —$(CH_2)_2$— | 4-$OCH_2CH_2OH$ | 3-Cl |

The salts with hydrochloric acid, sulphuric acid, phosphoric acid, oxalic acid, maleic acid, fumaric acid and malonic acid may preferably be mentioned.

The compounds of the formula I can be prepared by the processes (a) to (f) mentioned above under 2.

If, in the process 2(a) 2-chloroacetyl-6-methoxypyridine is employed as halogenomethyl ketone of the formula II and 2-(4-methoxycarbonylphenyl)ethylamine is employed as amine of the formula III, process (a) may be represented by the following equation:

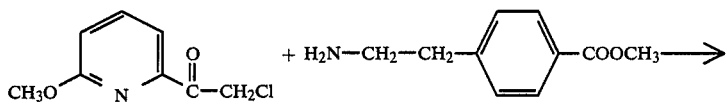

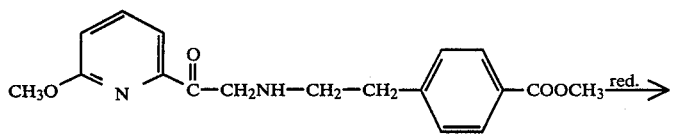

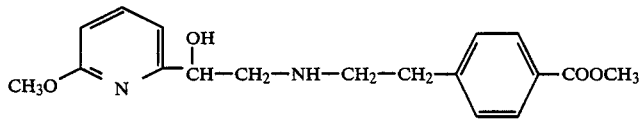

The compounds of the formula II are the subject-matter of German patent application No. P 3 615 293.5, corresponding to U.S. application Ser. No. 40,509 filed Apr, 20, 1987, now pending.

They are prepared by reacting the appropriate acetyl-substituted heteroaryl compounds with elementary halogen or with copper halides in a fashion which is known per se. The acetyl-substituted heteroaryl compounds are known from C. T. Gnewuch J. Med. Chem. 15, 1321 (1972) or U.S. patent specification No. 4,358,455, or can be prepared by the processes mentioned therein.

The substituents $R^1$, $R^2$ and $R^3$ in the formula II preferably have the preferred meanings mentioned above in the case of the compounds of the formula I. The following compounds of the formula II may be mentioned individually: 2-amino-3-chloro-5-pyridyl chloromethyl ketone, 2-amino-3-cyano-5-pyridyl chloromethyl ketone, 2,4-dichloro-3-amino-6-pyridyl bromomethyl ketone, 2-cyano-3-amino-6-pyridyl bromomethyl ketone, 3-amino-4-cyano-6-pyridyl bromomethyl ketone, 3-amino-4-cyano-6-pyridyl chloromethyl ketone, 2-cyano-3-amino-4-chloro-6-pyridyl bromomethyl ketone, 2-cyano-3-amino-4-chloro-6-pyridyl chloromethyl ketone, 2-chloro-3-amino-4-trifluoromethyl-6-pyridyl bromomethyl ketone, 2-trifluoromethyl-3-amino-4-cyano-6-pyridyl bromomethyl ketone, and 2-fluoro-3-amino-4-cyano-6-pyridyl chloromethyl ketone.

The amines of the formula III are known (cf., for example, EP-OS (European published specification) No. 70,133) or can be prepared analogously to known processes. The substituents $R^6$ to $R^{10}$ and X and Y preferably have the preferred meanings mentioned above in the case of the compounds of the formula I. The following compounds of the formula III may be mentioned individually:

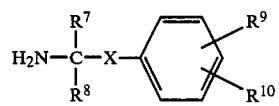

| $R^7$ | $R^8$ | X | $R^9$ | $R^{10}$ |
|---|---|---|---|---|
| H | $CH_3$ | $-CH_2-$ | 4-$OCH_2COOCH_3$ | H |
| $CH_3$ | H | $-CH_2-$ | 4-$OCH_2COOH$ | H |
| H | $CH_3$ | $-CH_2-$ | 4-$OCH_2CH_2OH$ | 3-$CH_3$ |
| H | H | $-(CH_2)_2-$ | 4-$OCH_2COOC_2H_5$ | 2-Cl |

The following reducing agents may be mentioned as reducing agents for carrying out the process 2(a): $H_2$/catalyst, where the following may be mentioned as examples of catalyst: $PtO_2$ and Pd/activated charcoal; complex metal hydrides, such as, for example, $LiAlH_4$, $NaBH_4$ and $NaBH_3CN$.

The following reducing agents are particularly preferably employed: $NaBH_4$ and $NaBH_3CN$.

The process 2(a) is carried out by mixing the compounds II and III in an approximately equimolar ratio in a diluent.

The reaction is preferably carried out at temperatures from $-20°$ C. to $+100°$ C.

The reaction is preferably carried out at atmospheric pressure.

All inert organic solvents are used as diluent. These include, in particular, aliphatic and aromatic hydrocarbons, such as pentane, hexane, cyclohexane, petroleum ether, ligroin, benzene and toluene; chlorinated hydrocarbons, such as methylene chloride, ethylene chloride and chloroform; ethers, such as diethyl ether and glycol dimethyl ether; nitriles, such as acetonitrile, propionitrile and benzonitrile; and alcohols, such as methanol, ethanol and n- and i-propanol.

Alcohols are preferred, it being possible for the reduction to be carried out without isolation of the intermediates.

If, in the process 2(b), 5-methoxypyridine 3-epoxide is employed as epoxide of the formula IV and 3-(4-ethoxycarbonylmethoxyphenyl)-2-aminopropane is employed as amine of the formula III, the process 2(b) may be represented by the following equation:

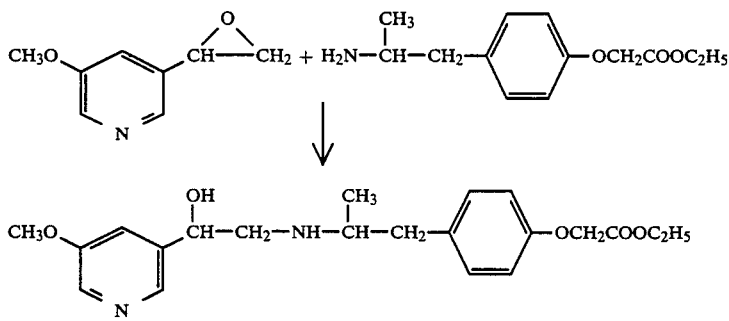

The epoxides of the formula IV are the subject-matter of German patent application No. P 3 615 293.5, supra. They are prepared in a manner which is known per se, by reacting halogenoethyl compounds of the formula

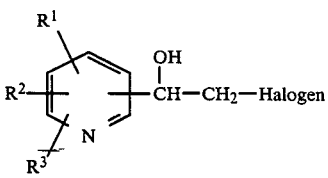

in which

R¹, R² and R³ have the meanings mentioned in the case of the compounds of the formula I,
with bases, or reacting the appropriate aldehydes of the formula

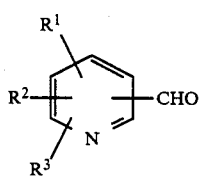

with reagents which transfer methyl groups, in the presence of bases under the conditions of the Corey epoxidization (E. J. Corey, J.A.C.S 87, 1353 (1955)).

The aldehydes are obtained by oxidizing the appropriate alcohols of the formula

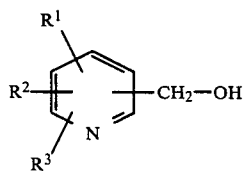

or reducing the appropriate acyl chlorides of the formula

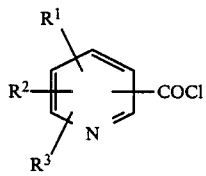

The alcohols and acyl chlorides are known.

The following expoxides may be mentioned individually: 2-amino-3-chloropyridine 5-epoxide, 2-amino-3-cyanopyridine 5-epoxide, 2,4-dichloro-3-aminopyridine 6-epoxide, 2-chloro-3-amino-4-cyanopyridine 6-epoxide, 2-cyano-3-amino-4-chloropyridine 6-epoxide, 2-cyano-3-aminopyridine 6-epoxide, 2-chloro-3-amino-4-trifluoromethylpyridine 6-epoxide, and 2-bromo-3-amino-4-cyanopyridine 6-epoxide.

The process (b) is carried out by reacting approximately equimolar amounts of the epoxide of the formula IV and of the amine of the formula III in a diluent.

In general, an excess of amine (1–3 molar, preferably 1–1.5 molar), relative to the epoxide of the formula IV, is used.

The reaction is carried out at temperatures from +20° to +150° C.

The reaction is preferably carried out at atmospheric pressure.

All inert organic solvents serve as diluents. These include, in particular, aliphatic and aromatic, optionally halogenated hydrocarbons, such as pentane, hexane, heptane, cyclohexane, petroleum ether, benzine, ligroin, benzene, toluene, methylene chloride, ethylene chloride, chloroform, carbon tetrachloride, chlorobenzene and o-dichlorobenzene, furthermore ethers, such as diethyl and dibutyl ether, glycol dimethyl ether and diglycol dimethyl ether, tetrahydrofuran and dioxane, furthermore nitriles, such as acetonitrile and benzonitrile, amides, such as dimethylformamide, and alcohols, such as methanol, ethanol, n- and i-propanol.

Alcohols are preferred.

If, in the process 2(c), 5-methoxy-3-(1-hydroxy-2-chloroethyl)pyridine is employed as the β-halogenomethyl compound of the formula V and 2-(4-methoxyphenyl)-1-methylethylamine is employed as amine of the formula III, the process (c) may be represented by the following equation:

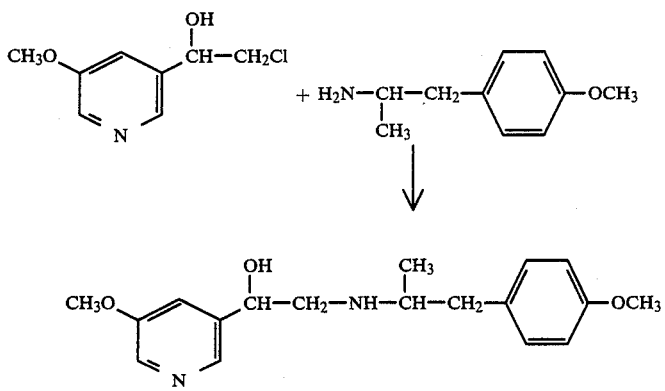

The β-halogenoethyl compounds of the formula V are the subject-matter of German patent application No. P 3 615 293.5, supra, and are obtained by reducing the appropriate halogenomethyl ketones or reacting the appropriate heteroarylvinyl compounds with N-halogenoacetamides.

The following compounds of the formula V may be mentioned individually: 1-(2-amino-3-chloro-5-pyridyl)-2-chloroethanol, 1-(2-amino-3-cyano-5-pyridyl)-2-chloroethanol, 1-(2,4-dichloro-3-amino-6-pyridyl)-2-chloroethanol, 1-(2-chloro-3-amino-4-cyano-6-pyridyl)-2-chloroethanol, 1-(2-cyano-3-amino-4-chloro-6-pyridyl)-2-bromoethanol, 1-(2-cyano-3-amino-6-pyridyl)-2-chloroethanol, 1-(3-amino-4-cyano-6-pyridyl)-2-bromoethanol, 1-(2-chloro-3-amino-4-trifluoromethyl-6-pyridyl)-2-chloroethanol, and 1-(2-cyano-3-amino-4-fluoro-6-pyridyl)-2-bromoethanol.

The process 2(c) is carried out by reacting the beta-halogenoethyl compound of the formula V with excess amine of the formula III, if appropriate in the presence of a diluent.

The reaction is carried out at temperatures from +20 to +150° C.

The reaction is carried out at atmospheric pressure or under increased pressure.

All inert organic solvents serve as diluents. These include, in particular, aliphatic and aromatic, optionally halogenated hydrocarbons, such as pentane, hexane, cyclohexane, benzene, toluene, methylene chloride and chloroform, furthermore ethers, such as diethyl ether, tetrahydrofuran and dioxane, in addition nitriles, such as acetonitrile and benzonitrile, furthermore amides, such as dimethylformamide, and furthermore alcohols, such as methanol, ethanol and n- and i-propanol.

Alcohols are preferably employed.

If, in the process 2(d), 5-fluoro-3-(1-hydroxy-2-aminoethyl)-pyridine is employed as compound of the formula VI and (3-chloro-4-methoxyphenyl)-acetone is employed as compound of the formula VII, the process (d) may be represented by the following equation:

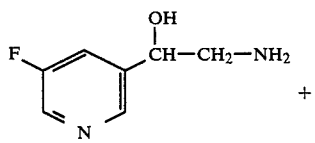

+

-continued

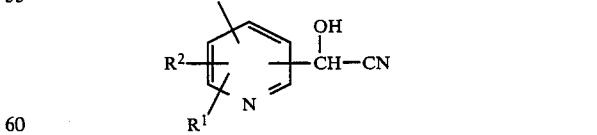

The compounds of the formula VI are the subject-matter of German patent application No. P 3 615 293.5, supra and can be prepared by reducing the appropriate nitro compounds. The nitro compounds are known (K. W. Merz Arch. Pharm. 1964, 10) or can be prepared analogously to known processes.

The following compounds of the formula VI may be mentioned individually: 1-(2-amino-3-chloro-5-pyridyl)-2-aminoethanol, 1-(2-amino-3-cyano-5-pyridyl)-2-aminoethanol, 1-(2,4-dichloro-3-amino-6-pyridyl)-2-aminoethanol, 1-(2-chloro-3-amino-4-cyano-6-pyridyl)-2-aminoethanol, 1-(2-cyano-3-amino-6-pyridyl)-2-aminoethanol, and 1-(2-chloro-3-amino-4-trifluoromethyl-6-pyridyl)-2-aminoethanol.

They, in the cases where the radicals $R^1$, $R^2$ and $R^3$ in the formula VI do not simultaneously represent hydrogen and $R^4$ represents OH, can be prepared by reducing compounds of the formula XIV $$R^3 \text{—} \underset{R^1}{\underset{N}{\bigodot}} \text{—} \underset{\underset{CH-CN}{|}}{\overset{OH}{|}} \quad (XIV)$$

in which
 $R^1$, $R^2$ and $R^3$ have the meanings mentioned in the case of the compounds of the formula I, with the proviso that the radicals $R^1$, $R^2$ and $R^3$ may not all simultaneously represent hydrogen.

The compounds of the formula XIV are new. They are obtained by reacting aldehydes of the formula XII

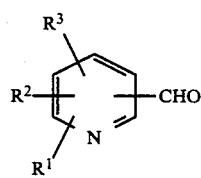 (XII)

in which

R¹, R² and R³ have the meaning mentioned in the case of the compounds of the formula I, with the proviso that the radicals R¹, R² and R³ may not all simultaneously represent hydrogen, with hydrogen cyanide or the salts thereof, or with the cyanohydrins of lower aliphatic ketones.

If, in the preparation of the compounds of the formula VI, 2-chloro-4-pyridyl-cyanohydrin is employed as compound of the formula XIV, the process may be represented by the following equation:

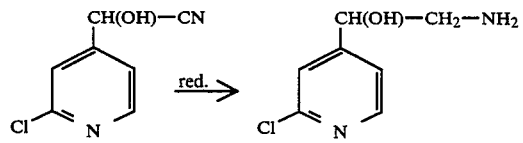

The compounds of the formula XIV are new. Their preparation is described below. The substituents R¹, R² and R³ in the compounds XIV have the preferred meanings mentioned in the case of the compounds of the formula I, where R¹, R² and R³ may not simultaneously represent hydrogen. The following compounds of the formula XIV may be mentioned individually: (2,6-dichloro-4-pyridyl)-cyanohydrin, (2-amino-5-pyridyl)-cyanohydrin, (2-amino-3-chloro-5-pyridyl)-cyanohydrin, (3-amino-6-pyridyl)-cyanohydrin, (2-chloro-3-amino-6-pyridyl)-cyanohydrin and (2,4-dichloro-3-amino-6-pyridyl)-cyanohydrin.

The process is carried out by reducing the compound XIV in a diluent.

The reaction is carried out at temperatures from 0° C. to 150° C.

The reaction is carried out at atmospheric pressure or at increased pressure.

Depending on the reducing agent, water or organic solvents, or mixtures thereof, serve as diluents. The organic solvents include aliphatic and aromatic, optionally halogenated hydrocarbons, such as pentane, hexane, cyclohexane, benzene, toluene, methylene chloride, ethylene chloride, chloroform and chlorobenzene, furthermore ethers, such as diethyl ether, tetrahydrofuran and dioxane, in addition nitriles, such as acetonitrile and benzonitrile, amides, such as dimethylformamide, and alcohols, such as methanol and ethanol.

The following serve as reducing agents: H₂/catalyst, where PtO₂, for example, may be mentioned as catalyst; alkali metal and alkaline earth metal amalgams, such as, for example, sodium amalgam; non-noble metals in the presence of hydrochloric acid, such as, for example, zinc/hydrochloric acid; complex metal hydrides, such as, for example, LiAlH₄; and boranes, such as, for example, diborane.

As already stated, the compounds of the formula XIV are new.

If, for the preparation thereof, 2-fluoropyridine-5-aldehyde is employed as compound of the formula XII, the process may be represented by the following equation:

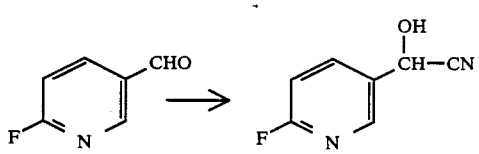

The preparation of the aldehydes of the formula XII has already been described (above) in the case of process (2). The substituents R¹, R² and R³ in the formula XII have the meanings mentioned in the case of the compounds of the formula I, where R¹, R² and R³ may not simultaneously represent hydrogen. The following compounds of the formula XII may be mentioned individually: 2,6-dichloropyridine-4-aldehyde, 2-aminopyridine-5-aldehyde, 2-amino-3-chloropyridine-5-aldehyde, 3-aminopyridine-6-aldehyde, 2-chloro-3-aminopyridine-6-aldehyde and 2,4-dichloro-3-aminopyridine-6-aldehyde.

The process is carried out by reacting, in a fashion known from the literature, the aldehydes of the formula XII, or the hydrogen sulphite-addition products thereof, with hydrogen cyanide or the salts thereof, or lower aliphatic ketone cyanohydrins (P. Kurtz, in Houben-Weyl, Volume VIII, p. 274 ff).

The compounds of the formula VII are known (cf., for example, EP-OS (European Published Specification) 23,385), or can be prepared analogously to known compounds. The substituents R⁸ to R¹⁰ and X and Y have the abovementioned meanings.

The following compounds of the formula VII may be mentioned individually:

$$R^8-\overset{O}{\underset{\|}{C}}-X-Y-\phenyl{R^9}{R^{10}}$$

| R⁸ | X | Y | R⁹ | R¹⁰ |
|---|---|---|---|---|
| H | —CH₂— | — | 4-COOCH₃ | H |
| CH₃ | —CH₂— | — | 4-OCH₂COOCH₃ | H |
| CH₃ | —CH₂— | — | 4-OCH₂CH₂OH | 3-Cl |
| CH₃ | —(CH₂)₂— | O | 4-COOH | 2-CH₃ |
| H | —CH₂— | O | 4-OCH₂COOH | H |

The process 2(d) is carried out by placing approximately equimolar amounts of the compounds of the formulae VI and VII in a diluent and reducing the mixture.

The reaction is carried out at temperatures from 0° C. to 150° C.

The reaction is preferably carried out at atmospheric pressure.

All inert organic solvents serve as diluents. These include aliphatic and aromatic, optionally halogenated hydrocarbons, such as pentane, hexane, cyclohexane, benzene, toluene, methylene chloride, ethylene chloride, chloroform and chlorobenzene, furthermore ethers, such as diethyl ether, tetrahydrofuran and dioxane, in addition nitriles, such as acetonitrile and benzonitrile, amides, such as dimethylformamide, and alcohols, such as methanol and ethanol.

The following serve as reducing agents: H₂/catalyst, where PtO₂, for example, may be mentioned as catalyst;

and complex metal hydrides, such as, for example, LiAlH$_4$, NaBH$_4$ and NaBH$_3$CN.

If, in the process 2(e), 5-methyl-3-pyridylglyoxal is employed as compound of the formula VIII and 2-(3-bromo-4-methoxyphenyl)-ethylamine is employed as amine of the formula IX, the process (e) may be represented by the following equation:

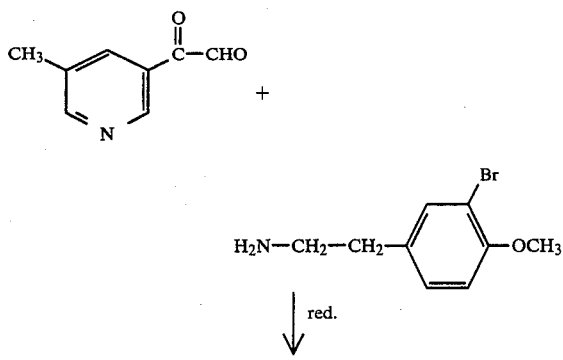

The preparation of the compounds of the formula VIII has already been described in the case of process 2b. The compounds of the formula IX are known (cf., for example, EP-OS (European Published Specification) 70,133), or can be prepared analogously to known compounds.

The substituents R$^1$, R$^2$ and R$^3$ in the formula VIII preferably have the preferred meanings mentioned above in the case of the compounds of the formula I. The following compounds of the formula VIII may be mentioned individually: 2-amino-3-chloro-5-pyridylglyoxal, 2-amino-3-cyano-5-pyridylglyoxal, 2,4-dichloro-3-amino-6-pyridylglyoxal, 2-cyano-3-amino-6-pyridylglyoxal, and 2-chloro-3-amino-4-trifluoromethyl-6-pyridylglyoxal, The process 2(e) is carried out by adding approximately the equivalent amount of the amine of the formula IX to the compound of the formula VIII in a diluent, and subsequently reducing.

The reaction is carried out at temperatures from 0° C. to 100° C.

The reaction is preferably carried out at atmospheric pressure.

All inert organic solvents serve as diluents. These include, in particular, aliphatic and aromatic, optionally halogenated hydrocarbons, such as pentane, hexane, heptane, cyclohexane, petroleum ether, benzine, ligroin, benzene, toluene, methylene chloride, ethylene chloride, chloroform, carbon tetrachloride, chlorobenzene and o-dichlorobenzene, furthermore ethers, such as diethyl and dibutyl ether, glycol dimethyl ether and diglycol dimethyl ether, tetrahydrofuran and dioxane, in addition esters, such as methyl acetate and ethyl acetate, furthermore nitriles, such as, for example, acetonitrile and propionitrile, benzonitrile and glutarodinitrile, additionally amides, such as, for example, dimethylformamide, dimethylacetamide and N-methylpyrrolidone, and also tetramethylene sulphone and hexamethylphosphoric triamide, and furthermore alcohols, such as methanol, ethanol and n- and i-propanol.

The following serve as reducing agents H$_2$/catalyst; where PtO$_2$ and Pd/charcoal may be mentioned as catalyst, and furthermore complex metal hydrides, such as LiAlH$_4$ and NaBH$_4$.

If, in the process 2(f), N-2-(4-methylphenyl)ethyl)(5-chloro-3-pyridyl)hydroxyacetamide is employed as compound of the formula X, the process may be represented by the following equation:

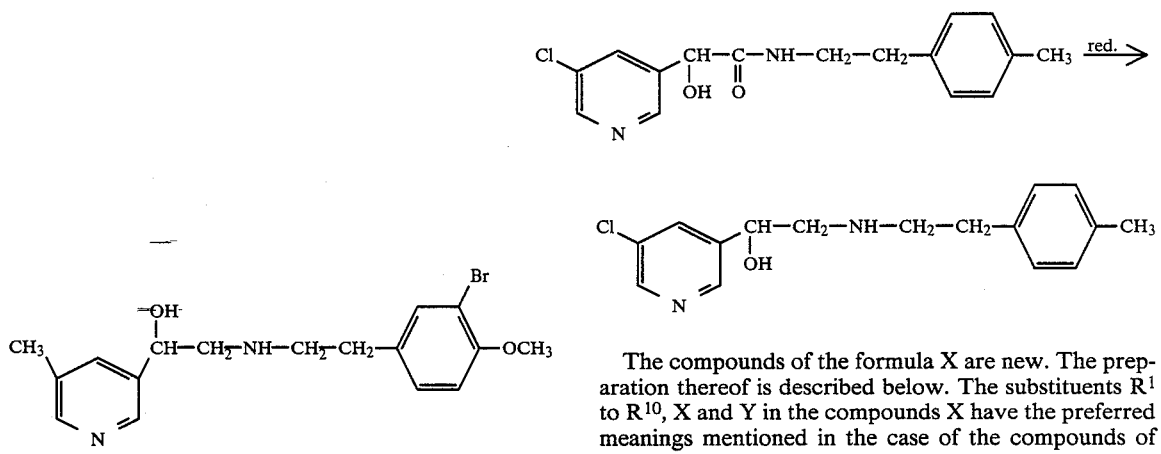

The compounds of the formula X are new. The preparation thereof is described below. The substituents R$^1$ to R$^{10}$, X and Y in the compounds X have the preferred meanings mentioned in the case of the compounds of the formula I. The following compounds of the formula X may be mentioned individually: N-(3-(4-methoxycarbonyl-methoxyphenyl)-2-propyl)-(2-amino-5-pyridyl)-hydroxyacetamide, N-(3-(4-ethoxycarbonylphenyl)-2-propyl)-(2-amino-3-chloro-5-pyridyl)hydroxyacetamide, N-(3-(4-methoxycarbonylmethoxyphenyl)-2-propyl)-(2-amino-3-cyano-5-pyridyl)hydroxyacetamide, N-(3-(4-ethoxycarbonylmethoxyphenyl)-2-propyl)-(3-amino-2,4-dichloro-6-pyridyl)hydroxyacetamide, N-(3-(4-methoxycarbonylphenyl)-2-propyl)-(2-cyano-3-amino-6-pyridyl)hydroxyacetamide, N-(3-(4-ethoxycarbonylmethoxyphenyl)-2-propyl)-(3-amino-4-cyano-6-pyridyl)hydroxyacetamide, N-(3-(4-methoxycarbonylphenyl)-2-propyl)-(2,6-dichloro-4-pyridyl)-hydroxyacetamide and N-(3-(4-methoxycarbonylmethoxyphenyl)-2-propyl)-(2,6-dichloro-4-pyridyl)hydroxyacetamide.

The process 2(f) is carried out by reacting the compound of the formula X with excess reducing agent in a diluent.

The reaction is carried out at temperatures from 0° C. to +150° C.

The reaction is preferably carried out at atmospheric pressure.

All inert organic solvents serve as diluents. These include, in particular, aliphatic and aromatic, optionally halogenated hydrocarbons, such as pentane, hexane, heptane, cyclohexane, petroleum ether, benzine, ligroin, benzene, toluene, methylene chloride, ethylene chloride, chloroform, carbon tetrachloride, chlorobenzene and o-dichlorobenzene, and furthermore ethers, such as diethyl and dibutyl ether, glycol dimethyl ether and diglycol dimethyl ether, tetrahydrofuran and dioxane.

Complex metal hydrides, such as $LiAlH_4$, and boranes, such as diborane, serve as reducing agents.

If, in the process (4), N-(2-(3-chloro-4-methylphenyl-)ethyl-(2-cyano-5-pyridyl)-acetoxyacetamide is employed as compound of the formula XI, the process may be represented by the following equation:

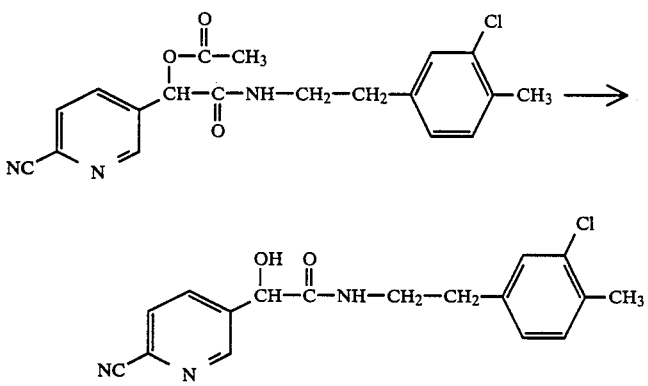

The compounds of the formula XI are new. Their preparation is described below. The substituents $R^1$ to $R^{10}$, X and Y in the compounds XI have the preferred meanings mentioned in the case of the compounds of the formula I. The following compounds of the formula XI may be mentioned individually: N-(3-(4-methoxycarbonylmethoxyphenyl)-2-propyl)-(2-amino-5-pyridyl)acetoxyacetamide, N-(3-(4-ethoxycarbonylphenyl)-2-propyl)-(2-amino-3-chloro-5-pyridyl)acetoxyacetamide, N-(3-(4-methoxycarbonylmethoxyphenyl)-2-propyl)-(2-amino-3-cyano-5-pyridyl)-acetoxyacetamide, N-(3-(4-ethoxycarbonylmethoxyphenyl)-2-propyl)-(3-amino-2,4-dichloro-6-pyridyl)acetoxyacetamide, N-(3-(4-methoxycarbonylphenyl)-2-propyl)-(2-cyano-3-amino-6-pyridyl)acetoxyacetamide, N-(3-(4-ethoxycarbonylmethoxyphenyl)-2-propyl)-(3-amino-4-cyano-6-pyridyl)acetoxyacetamide, N-(3-(4-methoxycarbonylphenyl)-2-propyl)-(2,6-dichloro-4-pyridyl)acetoxyacetamide and N-(3-(4-methoxycarbonylmethoxyphenyl)-2-propyl)-(2,6-dichloro-4-pyridyl)acetoxyacetamide.

Inorganic acids are used for cleaving off the acetyl group. These include hydrohalic acids, such as hydrochloric acid; sulphuric acid and phosphoric acid.

The process is carried out by treating the compound XI with excess aqueous solution of the inorganic acid in a diluent as solubilizer.

The reaction is carried out at temperatures from +20° C. to +150° C.

The process is preferably carried out at atmospheric pressure.

All inert organic solvents which are miscible with water may be used as diluents. These include ethers, such as tetrahydrofuran and dioxane; nitriles, such as acetonitrile; amides, such as dimethylformamide; alcohols, such as methanol and ethanol; and dimethyl sulphoxide.

If, in the process (6), 2-fluoro-pyridine-5-aldehyde is employed as compound of the formula XII and 3-(4-methoxyphenyl)-2-propyl isonitrile is employed as isonitrile of the formula XIII, the process may be represented by the following equation:

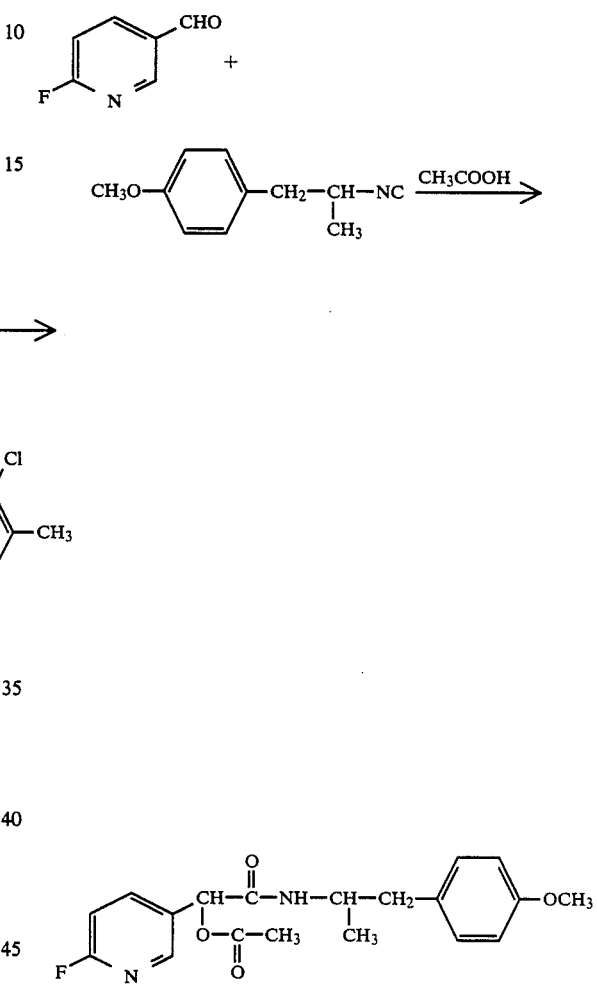

The preparation of the aldehydes of the formula XII has already been described (above) in the case of the process 2(b). The substituents $R^1$, $R^2$ and $R^3$ in the formula XII have the preferred meanings mentioned above in the case of the compounds of the formula I. The following compounds of the formula XII may be mentioned individually: 2-chloropyridine-4-aldehyde, 2-cyanopyridine-4-aldehyde, 2,6-dichloropyridine-4-aldehyde, 2-aminopyridine-5-aldehyde, 2-amino-3-chloropyridine-5-aldehyde, 2-amino-3-cyanopyridine-5-aldehyde, 2-chloro-3-aminopyridine-6-aldehyde, 2-cyano-3-aminopyridine-6-aldehyde, 2,4-dichloro-3-aminopyridine-6-aldehyde and 3-amino-4-cyanopyridine-6-aldehyde.

The isonitriles of the formula XIII are known (I. Ugi et al., Angew. Chem. 77 (1965), 492), or can be prepared analogously to known compounds. The substituents $R^7$ to $R^{10}$, X and Y have the preferred meanings mentioned above in the case of the compounds of the formula I. The following compounds of the formula XIII may be mentioned individually:

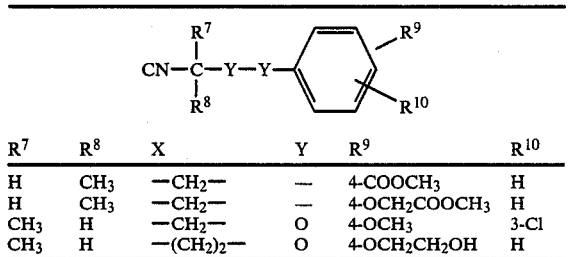

| R⁷ | R⁸ | X | Y | R⁹ | R¹⁰ |
|---|---|---|---|---|---|
| H | CH₃ | —CH₂— | — | 4-COOCH₃ | H |
| H | CH₃ | —CH₂— | — | 4-OCH₂COOCH₃ | H |
| CH₃ | H | —CH₂— | O | 4-OCH₃ | 3-Cl |
| CH₃ | H | —(CH₂)₂— | O | 4-OCH₂CH₂OH | H |

The process is carried out by reacting the compound XII with twice the molar amount of the isonitrile of the formula XIII and acetic acid in a diluent.

The reaction is carried out at temperatures from 0° C. to +150° C.

The reaction is preferably carried out at atmospheric pressure.

All inert organic solvents serve as diluents. These include, in particular, optionally halogenated aliphatic and aromatic hydrocarbons, such as pentane, hexane, cyclohexane, benzene, toluene, methylene chloride, chloroform and chlorobenzene; ethers, such as diethyl ether and tetrahydrofuran; and nitriles, such as acetonitrile and benzonitrile.

The active compounds are used as production promoters in livestock for promoting and accelerating growth and milk and wool production, and for improving the feed utilization and the meat quality, and for shifting the meat/fat ratio in favor of the meat. The active compounds are used for commercial stock, breeding stock, ornamental stock and hobby stock.

The commercial and breeding stock include mammals, such as, for example, cattle, pigs, horses, sheep, goats, rabbits, hares, fallow deer, pelt animals such as mink and chinchilla, poultry, such as, for example, chickens, geese, ducks, turkeys and doves, fish, such as, for example, carp, trout, salmon, eels, tench and pike, and reptiles, such as, for example, snakes and crocodiles.

The ornamental and hobby stock include mammals, such as dogs and cats, birds, such as parrots and canaries, and fish, such as ornamental and aquarium fish, for example goldfish.

Irrespective of the sex of the livestock, the active compounds are employed in all growth and production phases of the livestock. The active compounds are preferably employed in the intensive growth and production phase. Depending on the type of livestock, the intensive growth and production phase lasts from one month to 10 years.

The amount of active compounds which is administered to the livestock in order to achieve the desired effect may be varied substantially as a result of the favourable properties of the active compounds. This amount is preferably about 0.001 to 50 mg/kg, particularly 0.01 to 5 mg/kg of body weight per day. The suitable amount of the active compound and the suitable duration of the administration depend, in particular, on the type, of age, the sex, the health and the type of keeping and feeding of the livestock, and can easily be determined by any expert.

The active compounds are administered to the livestock by conventional methods. The type of administration depends, in particular, on the type, the behavior and the health of the livestock.

The administration is carried out orally or parenterally in formulations which are suitable for this or in pure form. Oral formulations are powders, tablets, granules, drenches, boli, feedstuffs, premixes for feedstuffs, and formulations for administration via the drinking water.

The oral formulations contain the active compound in concentrations of 0.01 ppm–100%, preferably 0.01 ppm–1%.

The active compounds may be administered once. However, the active compounds may also be administered temporarily or continuously over the entire growth and production phase or over part of the growth and production phase.

In the case of continuous administration, administration can be carried out once or several times daily at regular or irregular intervals.

The active compounds may be present in the formulations alone or mixed with other production-promoting active compounds, mineral feedstuffs, trace element compounds, vitamins, non-protein compounds which supply nitrogen, colorants, antioxidants, aromas, emulsifiers, flow auxiliaries, preservatives and tabletting auxiliaries.

Other production-promoting active compounds are: for example, antibiotics, such as tylosin and virginiamycin. Mineral feedstuffs are, for example, dicalcium phosphate, magnesium oxide and sodium chloride. Trace element compounds are, for example, iron fumarate, sodium iodide, cobalt chloride, copper sulphate and zinc oxide. Vitamins are, for example, vitamin A, vitamin D₃, vitamin E, B vitamins and vitamin C.

Non-protein compounds which supply nitrogen are, for example, biuret and urea. Colorants are, for example, carotinoids, such as citranaxanthin, zeaxanthin and capsanthin. Antioxidants are, for example, ethoxyquin and butylhydroxy-toluene. Aromas are, for example, vanillin. Emulsifiers are, for example, esters of lactic acid, and lecithin. Flow auxiliaries are, for example, sodium stearate and calcium stearate.

Preservatives are, for example, citric acid and propionic acid. Tabletting auxiliaries are, for example, ligninsulphonates and cellulose ethers.

The active compounds may also be administered together with the feed and/or with the drinking water.

The feed includes individual feedstuffs of vegetable origin, such as hay, beet and cereal by-products, individual feedstuffs of animal origin, such as meat, fats, milk products, bonemeal and fish products, individual feedstuffs such as vitamins, proteins, amino acids, for example DL-methionine and salts such as lime and sodium chloride. The feed also includes supplementary feed, prepared feed and compound feed. These contain individual feedstuffs in a composition which ensures balanced nutrition with respect to the energy and protein supply and with respect to the supply of vitamins, mineral salts and trace elements.

The concentration of the active compounds in the feed is normally about 0.01–500 ppm, preferably 0.1–50 ppm.

The active compounds may be added to the feed as such or in the form of premixes or feed concentrates.

The following is an exampole of the composition of a feed, for raising chicks, which contains 10 ppm of active compound according to the invention:

200 g of wheat, 340 g of corn, 361 g of soybean meal, 60 g of beef fat, 15 g of dicalcium phosphate, 10 g of calcium carbonate, 4 g of common salt with iodine, 7.5 g of vitamin mineral mixture and 2.5 g of the active compound premix mentioned below produce, after careful mixing, 1 kg of feed containing 10 ppm of active compound.

The following are contained in one kg of vitamin mineral: 600 I.U. of vitamin A, 100 I.U. of vitamin $D_3$, 10 mg of vitamin E, 1 mg of vitamin $K_3$, 3 mg of riboflavin, 2 mg of pyridoxin, 20 mcg of vitamin $B_{12}$, 5 mg of calcium pantothenate, 30 mg of nicotinic acid, 200 mg of choline chloride, 200 mg of $MnSO_4 \times H_2O$, 140 mg of $ZnSO_4 \times 7\ H_2O$, 100 mg of $FeSO_4 \times 7\ H_2O$ and 20 mg of $CuSO_4 \times 5\ H_2O$.

2.5 g of active compound premix contain, for example, 10 mg of active compound, 1 g of DL-methionine, and the rest is soybean meal.

The following is an example of the composition of a feed, for raising pigs, which contains 8 ppm of active compound according to the invention:

630 g of feed-grain meal (composed of 200 g of corn, 150 g of barley meal, 150 g of oat meal and 130 g of wheat meal), 80 g of fish meal, 60 g of soybean meal, 60 g of tapioca meal, 38 g of brewers' yeast, 50 g of vitamin mineral mixture for pigs, 30 g of linseed cake meal, 30 g of corn gluten feed, 10 g of soy oil, 10 g of sugar cane molasses and 2 g of active compound premix (composition, for example, as in the case of chick feed) produce, after careful mixing, 1 kg of feed containing 8 ppm of active compound.

The feed mixtures mentioned are balanced for raising and fattening of, preferably, chicks or pigs, but they can also be used, in the same or a similar composition, for feeding other livestock.

EXAMPLE A

Rat feeding experiment

Female laboratory rats weighing 90–110 g of the SPF Wistar (Hagemann breed) type are fed ad lib with standard rat feed to which is added the desired amount of active compound. Each experimental group is carried out using feed from the identical batch, so that differences in the composition of the feed cannot impair the comparability of the results.

The rats receive water ad lib.

12 rats form each experimental group and are fed with feed to which the desired amount of active compound is added. A control group receives feed without active compound. The average body weight and the scattering in the body weights of the rats is the same in each experimental group, so that comparability of the experimental groups with one another is ensured.

During the 13-day experiment, the increase in weight and the consumption of feed are determined and the relative increase in weight compared to the untreated control is calculated.

The results which can be seen from the table are obtained:

TABLE 1

Rat feeding experiment

| Active compound Example No. | Active compound used ppm | Relative increase in weight % |
|---|---|---|
| 2 | 25 | 38 |
| 3 | 25 | 22 |
| 4 | 25 | 31 |
| 5 | 25 | 61 |
| 1 | 25 | 31 |
| 6 | 25 | 34 |

EXAMPLES

General procedure for process 2a

Preparation of the compounds of the formula I by process 2a 10 mmol of the compound of the formula II are added in portions to a solution of 10 mmol of the amine of the formula III in 15 ml of absolute ethanol at 0° C. The mixture is allowed to come to 10°–15° C. and stirred for a further one hour at this temperature. The mixture is then recooled to 0° C., and 600 mg (50 mmol) of sodium borohydride are added in portions. The mixture is stirred overnight at room temperature. After addition of 20 ml of water, the mixture is stirred for 30 minutes, evaporated, and distributed between water and ethyl acetate. The organic phase is dried over sodium sulphate and evaporated. The residue is recrystallized.

General procedure for process 2b

Preparation of the compounds of the formula I by process 2b 0.1 mol of the compound of the formula IV and 0.11 mol of the amine of the formula III are refluxed overnight in 200 ml of methanol. The solvent and excess amine are stripped off and the residue is recrystallized.

General procedure for process 2c

Preparation of the compounds of the formula I by process 2c 10 mmol of the compound of the formula V are dissolved in 150 ml of ethanol, and 20 mmol of the amine of the formula III are added, and the mixture is refluxed for 18 hours. The solvent and excess amine are then stripped off, and the residue is taken up in 100 ml of dry ether. The insoluble amine hydrohalide is filtered off, and the ethereal solution is washed with water, dried over sodium sulphate and evaporated. The crude product is recrystallized.

General procedure for process 2d

Preparation of the compounds of the formula I by process 2d 22 mmol of the carbonyl compound of the formula VII are added to 22 mmol of the compound VI in 10 ml of absolute ethanol at 0°–5° C. The mixture is allowed to come to room temperature and stirred for a further 30 minutes. The solution is then added to 0.15 g of Adams catalyst (prehydrogenated in 10 ml of absolute ethanol), and the mixture is hydrogenated for 4–5 hours at 40° C. and 50 atm pressure of hydrogen. After filtering off the catalyst, the filtrate is evaporated, and the residue is recrystallized.

General procedure for process 2e

Preparation of the compounds of the formula I by process 2e 15 mmol of the amine of the formula IX are added dropwise to the solution of 10 mmol of the compound of the formula VIII in 50 ml of ethanol at 10°–15° C. The mixture is allowed to come to room temperature, and stirred for a further 15 minutes. The mixture is then diluted with a further 100 ml of ethanol, and 80 mmol of sodium borohydride are added in portions at 0°–5° C. The mixture is allowed to come to room temperature and stirred overnight. 200 ml of water are then added at 10° C., the mixture is stirred for 30 minutes, the ethanol is evaporated off, and the residue is extracted three times with 50 ml of dichloromethane in each case. The combined organic phases are washed with 100 ml of water, dried over sodium sulphate and evaporated.

General procedure for process 2f

Preparation of the compounds of the formula I by process 2f 2.3 mmol of the compound X in 30 ml of absolute tetrahydrofuran are added dropwise to 12.4 ml of a 1M solution of borane in tetrahydrofuran. The mixture is refluxed for 1 hour and diluted with ice water, and 50 ml of 1N hydrochloric acid are added. After evaporating off the organic solvent, the acidic aqueous solution is extracted twice with 30 ml of ether in each case, then rendered alkaline using saturated sodium carbonate solution and extracted three times with 30 ml of ethyl acetate in each case. The combined extracts are dried over sodium sulphate and evaporated.

The following compounds are prepared analogously to the abovementioned processes 2a–2f:

General procedure for process 4

Preparation of the compounds of the formula X by process 4

A suspension of 10 mmol of the compound XI in a mixture of 37 ml of methanol, 37 ml of water and 18 ml of 2.5N hydrochloric acid is heated at boiling for one hour. The methanol is then stripped off, and the precipitated solid is filtered off under suction.

General procedure for process 6

Preparation of compounds of the formula XI by process 6

A mixture of 10 mmol of the compound XII, 20 mmol of the compound XIII and 20 mmol of glacial acetic acid in 50 ml of dry chloroform is refluxed for two hours. then washed with 5% strength aqueous NaHCO$_3$ solution, dried over Na$_2$SO$_4$ and evaporated.

Example of the preparation of compounds of the formula VI:

1-(2,6-dichloro-4-pyridyl)-2-aminoethanol 230 ml (230 mmol) of a 1M solution of borane in tetrahydrofuran are added dropwise to a solution of 11.4 g (56 mmol) of (2,6-dichloro-4-pyridyl)-cyanohydrin in 200 ml of absolute tetrahydrofuran at room tem-

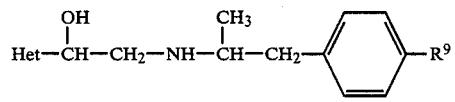

| Example No. | Het | R$^9$ | $^1$H NMR (CDCl$_3$, δ[ppm]) |
|---|---|---|---|
| 1 | 2-Pyridyl | COOCH$_3$ | 1.05 (d, 3H); 2.6–3.15 (m, 5H); 3.9 (s, 3H); 4.75 (m, 1H); 7.1–7.4 (m, 4H); 7.7 (m, 1H); 7.9 (m, 2H); 8.5 (m, 1H). |
| 2 | 3-Pyridyl | COOCH$_3$ | 1.05 (dd, 3H); 2.1 (s(broad)1H); 2.5–3.05 (m, 6H); 3.9 (s, 3H); 4.6 (m, 1H); 7.95 (m, 2H); 8.5 (m, 2H). |
| 3 | 4-Pyridyl | COOCH$_3$ | 1.1 (dd, 3H); 2.25–3.1 (m, 6H); 3.95 (m, 3H); 4.6 (m,H); 7.2 (m, 3H); 8.0 (m, 3H); 8.5 (m, 2H). |
| 4 | 2-Pyridyl | OCH$_2$COOCH$_3$ | 1.05 (dd, 3H); 2.5–3.2 (m, 5H); 3.8 (s, 3H); 4.6 (s, 2H); 4.7 (m, 1H); 6.85 (m, 2H); 7.0 (m, 2H); 7.2 (m, 1H); 7.4 (m, 1H); 8.5 (m, 1H). |
| 5 | 3-Pyridyl | OCH$_2$COOCH$_3$ | 1.1 (d, 3H); 2.5–3.2 (m, 6H); 3.8 (s, 3H); 4.6 (s, 2H), 4.7 (m, 1H); 6.85 (m, 2H); 7.0–7.2 (m, 3H); 7.7 (m, 1H); 8.5 (m, 2H). |
| 6 | 4-Pyridyl | OCH$_2$COOCH$_3$ | 1.05 (d, 3H); 2.5–3.05 (m, 5H); 3.8 (s, 3H); 4.6 (m, 1H); 4.65 (s, 2H); 6.8 (m, 2H); 7.0–7.3 (m, 4H); 8.5 (m, 2H). |
| 7 | 2,6-Dichloro-4-pyridyl | OCH$_2$CH$_2$OH | 1.1(dd,3H); 2.2 (s (broad), 1H); 2.5–3.1 (m, 5H); 4.0 (dd, 2H); 4.1 (dd, 2H); 4.6 (m, 1H); 6.8–7.2 (m, 6H). |
| 8 | 2-Amino-3-chloro-5-pyridyl | OCH$_2$CH$_2$OH | 1,1 (d, 3H); 2.2 (s(broad), 1H); 2.5–3.0 (m, 5H); 4.0 (dd, 2H); 4.5 (m, 1H); 5.0 (s (broad), 2H); 6.9 (m, 2H; 7.1 (m, 2H); 7.5 (m, 1H); 7.8 (m, 1H). |
| 9 | 2-Amino-3-chloro-5-pyridyl | OCH$_2$COOCH$_3$ | 1.1 (dd, 3H); 2.1 (s (broad), 1H); 2.5–3.0 (m, 5H); 3.8 (s, 3H); 4.5 (m, 1H); 4.6 (s, 2H); 4.9 (s(broad), 2H); 6.9 (m, 2H); 7.1 (m, 2H); 7.5 (m, 1H); 7.9 (m, 1H). |
| 10 | 2-Chloro-4-pyridyl | OCH$_2$CH$_2$OH | 1.1 (d, 3H); 2.2 (s (broad), 1H); 2.5–3.0 (m, 5H); 3.9 (dd, 2H); 4.1 (dd, 2H); 4.6 (m, 1H); 6.9–7.2 (m, 6H); 8.3 (m, 1H). | perature. When the addition is complete, the mixture is refluxed for one hour, then stirred overnight at room temperature. After acidification to pH 1 using concentrated hydrochloric acid, the mixture is stirred for 30 minutes and evaporated. The residue is taken up in a little water, filtered, adjusted to pH 3 using dilute sodium hydroxide solution, and washed with ethyl acetate (3×50 ml). The mixture is then rendered alkaline, and the product is extracted with ethyl acetate (3×100 ml). After drying and evaporation, 9.1 g (73%) are obtained, melting point 120° C. (decomposition).

Example of the preparation of the compounds of the formula XIV:

(2,6-dichloro-4-pyridyl)cyanohydrin 10 ml of 40% strength aqueous sodium hydrogen sulphite solution are added to a solution of 5 g (28.4 mmol) of 2,6-dichloropyridine-4-aldehyde in 30 ml of ether. 3.85 g of sodium cyanide in the form of a saturated aqueous solution are then added in one portion. After stirring for one hour, the ethereal phase is separated off, and the aqueous phase is extracted again with 20 ml of ether. The combined organic phases are dried and evaporated. Yield: 5.7 g (quantitative), melting point 140° C. (decomposition).

It is understood that the specification and examples are illustrative but not limitative of the present invention and that other embodiments within the spirit and scope of the invention will suggest themselves to those skilled in the art.

We claim:

1. A method of promoting the growth or production or shifting the meat/fat ratio of commercial stock, breeding stock, ornamental stock or hobby stock which comprises administering to such stock an effective amount therefor of a compound of the formula

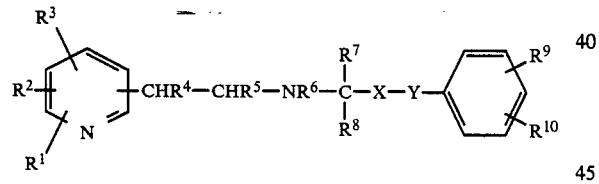

in which
$R^1$ and $R^3$ each independently represent hydrogen, $C_{1-4}$-alkyl, fluorine, chlorine, bromine, $C_{1-4}$-halogenoalkyl, hydroxyl, cyano, $C_{1-4}$-alkoxycarbonyl, mono- or di-$C_{1-4}$-alkylaminocarbonyl, $C_{1-6}$-alkoxy, $C_{1-6}$-halogenoalkoxy, $C_{1-6}$-halogenoalkylthio or —$NHSO_2$-$C_{1-6}$-alkyl,
$R^2$ represents hydrogen, hydroxyl, $C_{1-6}$-alkoxy or the —$NR^{11}R^{12}$ radical,
$R^4$ represents OH, $C_{1-6}$-alkoxy and acyloxy or represents oxycarbonyl-$C_{1-6}$-alkyl, optionally substituted oxycarbonylphenyl, oxysulphonyl-$C_{1-6}$-alkyl or optionally substituted oxysulphonylphenyl,
$R^5$ represents hydrogen or $C_1$-$C_6$-alkyl,
$R^6$ represents hydrogen or optionally substituted $C_{1-6}$-alkyl,
$R^7$ represents hydrogen or $C_1$-$C_6$-alkyl,
$R^8$ represents hydrogen or $C_1$-$C_6$-alkyl,
X represents $C_1$-$C_6$-alkylene or a direct bond,
Y represents oxygen or a direct bond,
$R^9$ represents $C_1$-$C_6$-alkyl which is substituted by hydroxyl, $C_1$-$C_6$-alkoxy, $C_1$-$C_6$-acyloxy or the $NR^{13}R^{14}$ radical, or represents the $COR^{15}$ radical or the O—Z—$R^{16}$ radical,
Z represents $C_1$-$C_6$-alkylene, $C_2$-$C_6$-alkenylene or $C_2$-$C_6$-alkinylene,
$R^{10}$ represents hydrogen, halogen, $C_1$-$C_6$-alkyl, $C_1$-$C_6$-alkoxy, hydroxyl or the $COR^{15}$ radical,
$R^{11}$ represents hydrogen or $C_1$-$C_6$-alkyl,
$R^{12}$ represents hydrogen, $C_{1-6}$-alkylcarbonyl or optionally substituted phenylsulphonyl,
$R^{13}$ and $R^{14}$ each independently represent hydrogen or $C_1$-$C_6$-alkyl which is optionally substituted,
$R^{15}$ represents hydroxyl, $C_1$-$C_6$-alkoxy, or the $NR^{13}R^{14}$ radical, and
$R^{16}$ represents hydroxyl, $C_1$-$C_6$-alkoxy, $C_1$-$C_6$-acyloxy, the $NR^{13}R^{14}$ or the $COR^{15}$ radical said optional substituents being cyano, halogen, hydroxy, $C_1$-$C_4$-alkyl, $C_1$-$C_4$-halogenoalkyl, $C_1$-$C_4$-alkoxy, $C_1$-$C_4$-halogenoalkoxy, $C_1$-$C_4$-alkylthio, and $C_1$-$C_4$-halogenoalkylthio, unsubstituted phenyl or phenoxy or phenyl or phenoxy substituted by the above mentioned substituents and, in the case where the, substituents are on the phenyl radical, are methylenedioxy, ethylenedioxy, halogen-substituted methylenedioxy and halogen-substituted ethylenedioxy.

2. A method according to claim 1, in which
$R^1$ and $R^5$ each independently represent hydrogen, $C_{1-4}$-alkyl, halogen, cyano, hydroxyl, $C_{1-4}$-halogenoalkyl having 1 to 5 halogen atoms, $C_{1-4}$-alkoxy, $C_{1-4}$-halogenoalkoxy having 1 to 5 halogen atoms, $NHSO_2$—$C_{1-4}$-alkyl, —COO—$C_{1-4}$-alkyl, —$CONH_2$, —CONH—$C_{1-4}$-alkyl or —CON($C_{1-4}$-alkyl)$_2$,
$R^2$ represents hydrogen, OH, $C_{1-4}$-alkoxy or —$NR^{11}R^{12}$,
$R^3$ represents the radicals mentioned in the case of $R^1$,
$R^4$ represents OH or $C_{1-6}$-acyloxy,
$R^5$ represents hydrogen or $C_1$-$C_3$-alkyl,
$R^6$ represents hydrogen,
$R^7$ represents hydrogen,
$R^8$ represents hydrogen or $C_1$-$C_3$-alkyl,
X represents $C_1$-$C_3$-alkylene,
Y represents a direct bond,
$R^9$ represents $C_1$-$C_3$-alkyl which is substituted by hydroxyl, $C_1$-$C_3$-alkoxy, $C_1$-$C_3$-acyloxy, or the $NR^{13}R^{14}$ radical, the $COR^{15}$ radical or the O—Z—$R^{16}$ radical,
Z represents $C_1$-$C_4$-alkylene, $C_2$-$C_4$-alkenylene or $C_2$-$C_4$-alkinylene,
$R^{10}$ represents hydrogen, halogen, $C_1$-$C_4$-alkyl, $C_1$-$C_3$-alkoxy, hydroxyl or the $COR^{15}$ radical,
$R^{11}$ represents hydrogen or $C_1$-$C_3$-alkyl,
$R^{12}$ represents hydrogen or methyl,
$R^{13}$ represents hydrogen or $C_1$-$C_3$-alkyl,
$R^{14}$ represents hydrogen,
$R^{15}$ represents hydroxyl, $C_1$-$C_3$-alkoxy, or the $NR^{13}R^{14}$ radical, and
$R^{16}$ represents hydroxyl, $C_1$-$C_3$-alkoxy, $C_1$-$C_3$-acyloxy, the $NR^{13}R^{14}$ radical or the $COR^{15}$ radical.

3. A method according to claim 1, in which
$R^1$ and $R^3$ each independently represent hydrogen, $C_1$-$C_4$-alkyl, fluorine, chlorine, bromine, cyano, hydroxyl, $C_{1-4}$-halogenoalkyl having 1 to 5 halogen atoms, $C_{1-4}$-alkoxy, $C_{1-4}$-halogenoalkoxy having 1 to 5 halogen atoms, $NHSO_2$—$C_{1-4}$-alkyl, —COO—$C_{1-4}$-alkyl, —$CONH_2$, —CONH—$C_{1-4}$-alkyl or —CON($C_{1-4}$-alkyl)$_2$, $R^2$ represents hydrogen, OH, $C_{1-4}$-alkoxy or $-NR^{11}R^{12}$, $R^4$ represents OH or acetoxy, $R^5$ represents hydrogen, methyl or ethyl, $R^6$ represents hydrogen, $R^7$ represents hydrogen, $R^8$ represents hydrogen, methyl or ethyl, X represents methylene or ethylene, Y represents a direct bond, $R^9$ represents $C_1$-$C_3$-alkyl which is substituted by hydroxyl, methyl, acetoxy or the $NR^{13}R^{14}$ radical, the $COR^{15}$ radical or the $O-Z-R^{16}$ radical, Z represents methylene, ethylene, $C_2$-$C_4$-alkenylene or $C_2$-$C_4$-alkinylene, $R^{10}$ represents hydrogen, fluorine, chlorine, bromine, methyl, methoxy, hydroxyl or the $COR^{15}$ radical, $R^{11}$ represents hydrogen, methyl or ethyl, $R^{12}$ represents hydrogen or methyl, $R^{13}$ represents hydrogen, methyl or ethyl, $R^{14}$ represents hydrogen, $R^{15}$ represents hydroxyl, methoxy, ethoxy or the $NR^{13}R^{14}$ radical, and $R^{16}$ represents hydroxyl, methoxy, acetoxy, the $NR^{13}R^{14}$ radical or the $COR^{15}$ radical.

4. A method according to claim 1, in which the method comprises shifting the meat/fat ratio of said stock.

5. A method according to claim 4, in which
$R^7$ represents $C_1$-$C_6$-alkyl,
$R^8$ represents hydrogen, and
X represents methylene.

6. A method according to claim 4, in which
$R^9$ represents $C_1$-$C_6$-alkyl radical which is optionally substituted by hydroxy, $C_1$-$C_6$-alkoxy, $C_1$-$C_6$-acyloxy or the $NR^{13}R^{14}$ radical, or represents the $COR^{15}$ radical or the $-OZR^{16}$ radical, and
$R^{10}$ represents hydrogen.

7. A method according to claim 5, in which
$R^9$ represents $C_1$-$C_6$-alkyl radical which is optionally substituted by hydroxy, $C_1$-$C_6$-alkoxy, $C_1$-$C_6$-acyloxy or the $NR^{13}R^{14}$ radical, or represents the $COR^{15}$ radical or the $-OZR^{16}$ radical, and
$R^{10}$ represents hydrogen.

8. A method according to claim 5, in which
$R^7$ represents $C_1$-$C_6$-alkyl,
$R^8$ represents hydrogen, and
X represents methylene.

9. A method according to claim 8, in which
$R^9$ represents $C_1$-$C_6$-alkyl radical which is optionally substituted by hydroxy, $C_1$-$C_6$-alkoxy, $C_1$-$C_6$-acyloxy or the $NR^{13}R^{14}$ radical, or represents the $COR^{15}$ radical or the $-OZR^{16}$ radical, and
$R^{10}$ represents hydrogen.

10. A method according to claim 1, in which
$R^7$ represents $C_1$-$C_6$-alkyl,
$R^8$ represents hydrogen, and
X represents methylene.

11. A method according to claim 9, in which
$R^7$ represents $C_1$-$C_6$-alkyl,
$R^8$ represents hydrogen, and
X represents methylene.

12. A method according to claim 1, in which
$R^9$ represents $C_1$-$C_6$-alkyl radical which is optionally substituted by hydroxy, $C_1$-$C_6$-alkoxy, $C_1$-$C_6$-acyloxy or the $NR^{13}R^{14}$ radical, or represents the $COR^{15}$ radical or the $-OZR^{16}$ radical, and
$R^{10}$ represents hydrogen.

13. A method according to claim 12, in which
$R^7$ represents $C_1$-$C_6$-alkyl,
$R^8$ represents hydrogen, and
X represents methylene.

14. A method according to claim 1, in which
$R^1$ represents fluorine, chlorine or bromine,
$R^2$ represents hydrogen, and
$R^3$ represents hydrogen, fluorine, chlorine or bromine.

15. A method according to claim 1, in which
$R^1$ represents fluorine, chlorine or bromine,
$R^2$ represents hydrogen or the $-NR^{11}R^{12}$ radical, and
$R^3$ represents hydrogen, fluorine, chlorine or bromine.

* * * * *